(12) United States Patent
Giori

(10) Patent No.: US 7,270,860 B2
(45) Date of Patent: Sep. 18, 2007

(54) MULTILAYER CHLORINE-FREE FILM WITH BARRIER LAYER OF A POLYAMIDE BLEND AND OSTOMY POUCHES FORMED THEREFROM

(75) Inventor: Claudio Giori, Riverwoods, IL (US)

(73) Assignee: Hollister Incorporated, Libertyville, IL (US)

( * ) Notice: Subject to any disclaimer, the term of this patent is extended or adjusted under 35 U.S.C. 154(b) by 169 days.

(21) Appl. No.: 10/850,214

(22) Filed: May 20, 2004

(65) Prior Publication Data

US 2004/0228992 A1 Nov. 18, 2004

Related U.S. Application Data

(63) Continuation-in-part of application No. 10/128,923, filed on Apr. 24, 2002, now abandoned, which is a continuation of application No. 09/444,813, filed on Nov. 22, 1999, now abandoned.

(51) Int. Cl.
*A61F 5/445* (2006.01)
*A61L 28/00* (2006.01)

(52) U.S. Cl. ............... 428/35.7; 428/34.1; 428/35.2; 428/475.8; 428/476.1; 604/332

(58) Field of Classification Search ............ 428/35.2, 428/35.7, 36.7, 200, 220, 347, 349, 475.8, 428/476.1, 476.3, 476.6, 476.9, 520, 522–523, 428/34.1–34.3; 604/332, 343–344
See application file for complete search history.

(56) References Cited

U.S. PATENT DOCUMENTS

| | | | |
|---|---|---|---|
| 3,845,163 A | 10/1974 | Murch | 525/183 |
| 4,239,826 A | 12/1980 | Knott, II et al. | 428/36.7 |
| 4,254,169 A | 3/1981 | Schroeder | 428/36.6 |
| 4,572,854 A | 2/1986 | Dallmann et al. | 206/524.1 |
| 4,911,963 A | 3/1990 | Lustig et al. | 428/36.91 |
| 5,126,401 A * | 6/1992 | Chou | 525/58 |
| 5,212,246 A | 5/1993 | Ogale | 525/240 |
| 5,316,826 A | 5/1994 | Kotani et al. | 428/172 |
| 5,399,396 A | 3/1995 | Ohlsson et al. | 428/34.7 |
| 5,407,713 A | 4/1995 | Wilfong et al. | 428/34.1 |
| 5,455,091 A | 10/1995 | Oreglia et al. | 428/36.1 |

(Continued)

FOREIGN PATENT DOCUMENTS

CA 2122288 10/1994

(Continued)

OTHER PUBLICATIONS

European Search Report from European Application No. 04018844.3.

*Primary Examiner*—Rena Dye
*Assistant Examiner*—Sow-Fun Hon
(74) *Attorney, Agent, or Firm*—Marshall, Gerstein & Borun LLP

(57) ABSTRACT

A multilayer heat-sealable chlorine-free odor barrier film having relatively low modulus, high interlaminar strength, and low noise upon flexing is provided. The film comprises an odor barrier layer of an amorphous polyamide resin blended with an anhydride-modified olefinic polymer or copolymer. The film also includes at least one heat-sealable skin layer, preferably two such skin layers on opposite sides of said odor barrier layer, composed of an ethylene polymer or copolymer. Pouches formed of such multilayer films are also disclosed.

11 Claims, 1 Drawing Sheet

U.S. PATENT DOCUMENTS

| | | | |
|---|---|---|---|
| 5,470,624 A * | 11/1995 | Oreglia et al. | 428/36.1 |
| 5,496,295 A | 3/1996 | Wilfong et al. | 604/332 |
| 5,567,489 A | 10/1996 | Allen et al. | 428/34.1 |
| 5,643,375 A | 7/1997 | Wilfong et al. | 156/244.24 |
| 5,885,703 A | 3/1999 | Wilkie | 428/220 |
| 5,895,694 A | 4/1999 | Zavadsky et al. | 428/36.7 |
| 5,985,390 A | 11/1999 | DeGrand | 428/36.6 |
| 6,143,383 A | 11/2000 | Giori | 428/35.2 |
| 6,258,423 B1 | 7/2001 | Giori | 428/36.7 |
| 6,455,161 B1 * | 9/2002 | Regnier et al. | 428/412 |
| 2004/0052911 A1 | 3/2004 | Grund et al. | 426/125 |

FOREIGN PATENT DOCUMENTS

| | | |
|---|---|---|
| EP | 0 622 182 | 11/1994 |
| EP | 0 700 777 | 3/1996 |
| EP | 1 101 605 | 5/2001 |

* cited by examiner

MULTILAYER CHLORINE-FREE FILM WITH BARRIER LAYER OF A POLYAMIDE BLEND AND OSTOMY POUCHES FORMED THEREFROM

RELATED APPLICATION

This application is a continuation-in-part of application Ser. No. 10/128,923, now abandoned, filed Apr. 24, 2002, which in turn was a continuation of application Ser. No. 09/444,813 filed Nov. 22, 1999 now abandoned.

BACKGROUND AND SUMMARY

Films for ostomy applications should have good odor barrier properties and produce minimal noise when flexed or wrinkled to avoid embarrassment to users. Typically, films currently in use for ostomy applications utilize polyvinylidene chloride (PVDC) or copolymers of vinylidene chloride with a comonomer such as methylacrylate or vinylchloride as the gas barrier layer of a multilayer film. Such multilayer films have good resistance to odor transmission and are also relatively quiet; however, they are also believed to be hazardous to the environment when disposed of by incineration, a common practice in numerous countries. Chlorinated polymers generate hydrochloric acid as a byproduct of incineration and are believed to be a significant contributor to hydrochloric acid release from incinerator flue gases. Furthermore, chlorinated polymers are believed to form toxic dioxin derivatives as byproducts of incineration which are retained in the ashes and may possibly cause solid waste disposal problems.

Unfortunately, films formed of chlorine-free barrier resins tend to be stiffer and noisier than films utilizing conventional PVDC-based resins and do not match the quality of conventional chlorinated films for use in ostomy appliances. Thus, a need exists for a multilayer film which is chlorine-free, can be manufactured by coextrusion from readily available raw materials, is heat sealable, has high softness and low noise when flexed or wrinkled, and is impermeable to fecal odors.

U.S. Pat. No. 5,567,489 discloses a multilayer barrier film in which a chlorine-free barrier layer is composed of amorphous nylon, crystalline nylon, copolymers of ethylene and vinyl alcohol, or blends thereof. Although data presented in the patent indicate the multilayer films to be comparable in quietness to some chlorinated films in general commercial use, experience has revealed that such chlorine-free films are nevertheless significantly noisier than the chlorine-containing films commonly employed for the fabrication of ostomy pouches. The general observation is that chlorine-free barrier resins are high modulus, stiff materials that do not lend themselves to the production of low noise ostomy films. This is true of all nylon (polyamide) barrier resins, both crystalline and amorphous. It is true also of other known chlorine-free barrier resins such as hydrolyzed ethylene-vinylacetate copolymers, commonly known as ethylene-vinylalcohol copolymers, and copolymers of acrylonitrile or methacrylonitrile of high nitrile content, commonly known as nitrile resins.

The aforementioned U.S. patent specifically notes in column 1, lines 46-52, that multilayer films using nylon as a barrier layer are known for various uses, including the packaging of meats where oxygen and moisture barrier properties are important, but such films are taught to be biaxially oriented to improve puncture resistance, making them too noisy for use in ostomy applications.

Other references illustrating the current state of the art relating to chlorine-free multilayer films are U.S. Pat. Nos. 5,496,295, 5,643,375, 5,407,713, and 5,895,694.

An important aspect of this invention lies in the discovery that the noise properties of a multilayer film in which amorphous nylon (polyamide) is utilized for the odor barrier layer may be significantly reduced, without appreciably affecting the barrier properties, by blending the nylon with an anhydride-modified olefinic polymer or copolymer having a density of 0.95 g/cc or lower. The anhydride-modified olefinic polymer or copolymer should be present in the range of about 10% to 30%, preferably 15% to 25%, per total weight of the barrier layer.

The multilayer film includes at least one skin layer, preferably two such skin layers, consisting essentially of an ethylene polymer or copolymer, and an adhesive tie layer interposed between each skin layer and the blended amorphous nylon barrier layer. Each adhesive tie layer is primarily composed of an anhydride-modified ethylenic polymer, such as polyethylene or copolymer of ethylene and vinylacetate, containing anhydride groups capable of promoting interfacial adhesion with the polyamide-containing barrier layer.

The result is a heat-sealable multilayer film that is particularly useful for ostomy appliances because of its exceptional odor barrier properties while at the same time being relatively soft (low modulus) and quiet in relation to known chlorine-free films in which the odor barrier layer is formed entirely of nylon, ethylene-vinylalcohol copolymers, or nitrile resins. With regard to the generation of noise upon flexing, the chlorine-free multilayer films of this invention compare favorably with prior art ostomy films having chlorinated barrier layers. A pouch formed of the multilayer film of this invention therefore has properties comparable to those exhibited by high-quality pouches formed of chlorine-containing compositions but without the environmental shortcomings described above.

Other features, advantages and objects of the invention will become apparent from the specification and drawings.

DRAWINGS

DETAILED DESCRIPTION OF PREFERRED EMBODIMENTS

The multilayer chlorine-free film of the present invention may be produced using standard coextrusion techniques involving either casting or blowing. Preferably, the multilayer film has five layers—a chlorine-free barrier layer sandwiched between two heat-sealable skin layers with tie layers interposed between the skin and barrier layers—but the advantages of the invention may be at least partially achieved in a three-layer structure having a barrier layer and single skin and tie layers, or barrier layer and two skin layers without tie layers. The film may have more than five layers, for example, a seven-layer structure ABCDCBA could be made where D is the barrier layer, C is a tie layer, A is a skin layer, and B is an additional layer interposed between skin and tie layers. Asymmetric structures with different skin materials are possible and may provide different surface characteristics if so required.

Figure 1:
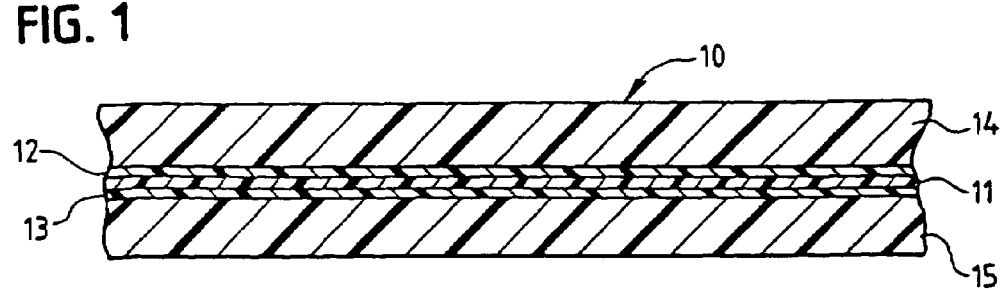
FIG. 1 is a schematic cross-sectional view of an embodiment of the multilayer barrier film of this invention.

FIG. 1 schematically illustrates a multilayer chlorine-free film 10 having an odor barrier layer 11 sandwiched between tie layers 12 and 13 and skin layers 14 and 15. The chlorine-free barrier layer 11 is essentially composed of a blend of amorphous polyamide (nylon) resin and an anhydride-modified olefinic polymer or copolymer. Unlike crystalline polyamides which are entirely aliphatic, amorphous polyamides have a partially aromatic structure and are typically produced by the condensation of an aliphatic diamine with an aromatic diacid, or combination of diacids, in molar amounts equivalent to the diamine used. While it is believed that any amorphous polyamide resin may be used, effective results have been obtained with a polyamide resin marketed as Selar PA3426 by DuPont Company. Selar PA3426 is understood to be substantially amorphous with a density of about 1.19 grams per cubic centimeter (g/cc). It has high melt strength and can be used under a broader range of processing conditions than conventional crystalline nylons. Selar PA3426 is produced by the condensation of hexamethylenediamine, terephthalic acid, and isophthalic acid such that 65% to 80% of the polymer units are derived from hexamethylene isophthalamide. For further information, reference may be had to 52 Fed. Reg. 26,667 (1987), the disclosure of which is incorporated by reference herein. A similar polyamide is marketed as Grivory 21 by EMS-Chemie of Switzerland.

The amorphous polyamide resin is the major constituent of the blend, comprising about 70% to 90% by weight of that blend. The anhydride-modified olefinic polymer or copolymer comprises about 10% to 30%, preferably 15% to 25% of the total weight of the barrier layer. The density of the anhydride modified olefinic polymer or copolymer should be no greater than 0.95 g/cc. Anhydride-modified olefinic polymers or copolymers with densities higher than 0.95 g/cc might still be effective as toughening agents but would not provide the reduction in film modulus and noise imparted by lower density polymers.

Where the olefinic polymer or copolymer is a copolymer of ethylene and at least one ester containing comonomer, or a blend thereof, modified (grafted or copolymerized) with 0.1 to 2% by weight of an unsaturated carboxylic anhydride (serving as a compatibilizing agent having amine reactive sites), the density of the modified olefinic copolymer may be as high as 0.95 glcc, but for an olefinic copolymer of ethylene and an alpha-olefin, or a blend thereof, similarly grafted or copolymerized with 0.1 to 2% of such anhydride, the density is preferably no higher than 0.89 glcc, and more preferably no higher than about 0.87 g/cc.

The olefinic polymer or copolymers can be functionalized by copolymerization or grafting with an unsaturated carboxylic anhydride. While it is believed that other unsaturated carboxylic anhydrides may be used to provide the functional groups, maleic anhydride is considered particularly effective for that purpose. The level of maleic anhydride needed to functionalize the olefinic polymer is quite low, usually less than 2% by weight. The density of the olefinic polymer is essentially unaffected by anhydride modification at these low levels. One example of an anhydride-modified copolymer of ethylene with an alpha olefin is Fusabond MN493D available from DuPont Company. Fusabond MN493D is an ethylene octene copolymer that is modified with 0.5% maleic anhydride and has a density of 0.869 g/cc. While it is known to function as a toughening agent for crystalline nylon, Fusabond MN493D performs an unexpected function here in decreasing modulus and noise of amorphous nylon without destroying or significantly reducing the odor barrier properties of layer 11.

As indicated, another suitable modifier may be formed from ethylene and at least one ester-containing comonomer, or a blend thereof, grafted or copolymerized with between 0.1 to 2% by weight of the unsaturated carboxylic anhydride, the anhydride content preferably being well under 0.5% by weight. The ester-containing comonomer is preferably an alkylacrylate, most preferably an ethylacrylate. One such copolymer is available from Atofina Chemicals, Inc., of France, under the designation Lotader 4720. Lotader 4720 is an ethylene-ethyl acrylate-maleic anhydride terpolymer with a density of 0.944 g/cc, an ethyl acrylate content of about 30% by weight and a maleic anhydride content of about 0.3% by weight.

Similar performance can be achieved with other anhydride-modified olefinic polymers of copolymers shaving comparable low density, such as ethylene-propylene copolymers and terpolymer (EPM and EPDM). EPM and EPDM have a density in the 0.85 to 0.86 g/cc range and are suitable for modification with maleic anhydride.

Due to the immiscible nature of these blends, mixing of the nylon with the anhydride-modified olefinic polymer is best conducted in a separate step using a twin screw compounder extruder with either corotating or counterrotating screws. This allows an intimate dispersion of the olefinic phase into the nylon phase. The compounded blend is extruded and cut into pellets which can then be used for extrusion into film.

Skin layers 14 and 15 are typically formed of an ethylene-based polymer or copolymer. A suitable resin is metallocene-catalyzed polyethylene with an alpha olefin comonomer such as the ethylene octene copolymer marketed under the designation Exact 8201 by Exxon Chemical. Also suitable as skin layers are copolymers of ethylene with vinyl esters such as ethylene vinyl acetate copolymer (EVA) available, for example, from the DuPont Company under the designation Elvax.

Tie layers 12 and 13 must be capable of bonding to both the core barrier layer and the adjacent layers. Polyethylene, ethylene vinyl acetate copolymers (EVA), or ethylene methyl acrylate copolymers (EMA), modified with functional anhydride groups are believed particularly suitable. EVA-based anhydride-modified resins such as Bynel 3860 or Bynel 3861, or polyethylene-based anhydride-modified resins such as Bynel 41E557, all available from DuPont Company, have been found suitable. The ability of these anhydride-modified resins to act as adhesion promoters is believed to be due to an interfacial reaction between the anhydride groups in the tie layer and the amine groups of nylon in the barrier layer.

The total thickness of the multilayer film, assuming five layers are present, should fall within the general range of about 2 to 5 mil, preferably about 3 to 4 mil. As to the barrier layer 11, its thickness should fall generally within the range of 0.1 to 0.5 mil with the lower limit being established by the capability of the extrusion process and the upper limit by the physical properties contributed by the barrier layer in achieving a multilayer film having low modulus and low noise characteristics. Preferably, the barrier layer thickness should fall within the range of about 0.2 to 0.3 mil, when factors such as odor barrier properties, softness, quietness, and ease of extrusion are all considered together. By contrast, the skin layers 14 and 15 are each considerably thicker than the barrier layer sandwiched between them. For example, each skin layer may have a thickness within the general range of about 0.5 to 2.5 mil, preferably 1 to 2 mil, which may be nearly one order of magnitude greater than the thickness of the odor barrier layer 11.

Figure 2:
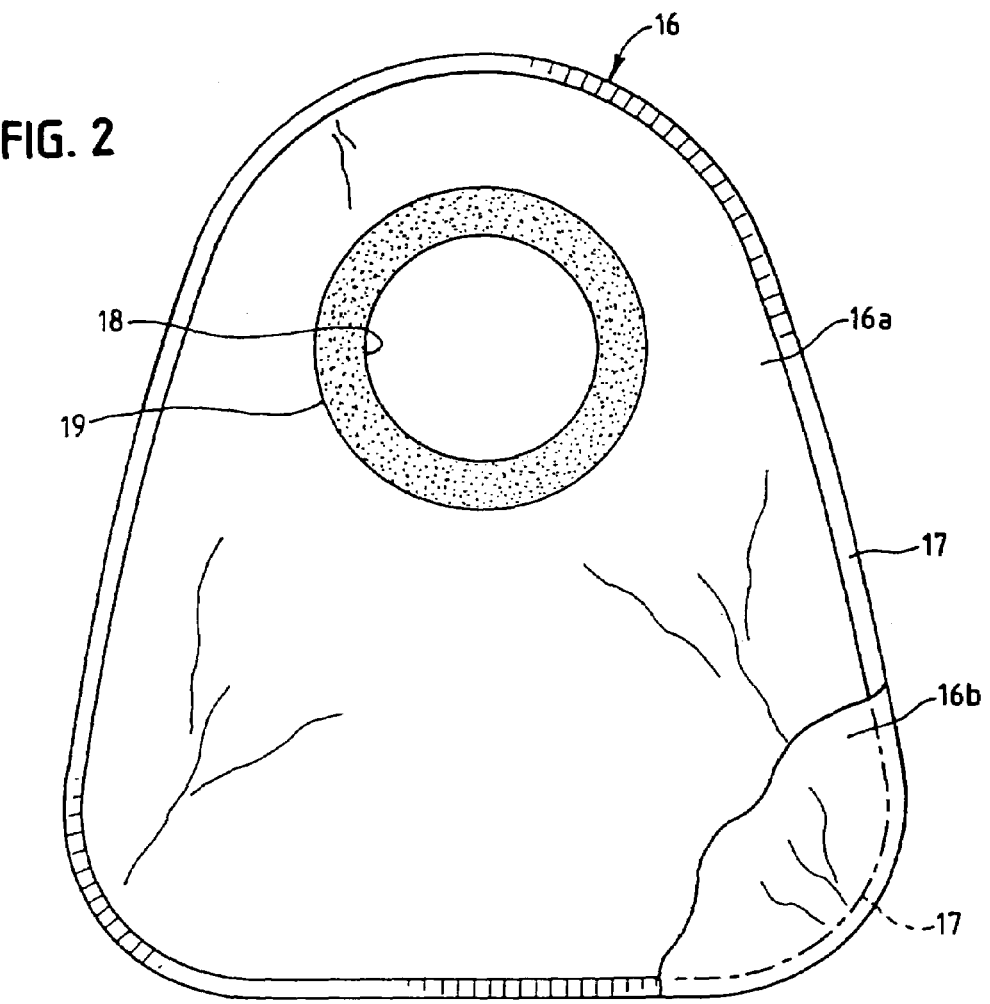
FIG. 2 is an elevational view of an ostomy pouch formed from the multilayer barrier film of FIG. 1.

FIG. 2 illustrates a typical ostomy pouch 16 having its walls 16a and 16b formed from the multilayer film of FIG. 1. The films are arranged with their heat sealable skin layers facing each other and sealed together along the outer periphery of the pouch as indicated at 17. One wall of the pouch has a stoma-receiving opening is formed therein and an adhesive attachment ring 19 is located about that opening for adhesive attachment to the peristomal skin surfaces of a patient. The pouch as shown is of the type generally referred to as a one-piece appliance but, if desired, a mechanical coupling ring may be substituted for adhesive ring 19, with the pouch therefore becoming one component of a two-piece ostomy appliance, all as well known in the art.

In order that the invention may be more readily understood, reference is made to the following examples which are intended to be illustrative of the invention, but are not intended to be limiting in scope.

EXAMPLE 1

This example illustrates the properties of blends of amorphous nylon (Selar PA3426, DuPont Company) with anhydride-modified polyolefin (Fusabond MN493D, DuPont Company). The two resins were compounded and pelletized using a twin screw compounder extruder. The compounded resins were then coextruded using a Killion extruder into a A/B/A three-layer film structure, wherein A was polyethylene and B was the nylon blend. Because of the absence of tie layers, it was possible to strip the polyethylene skin layers A from the nylon blend layer B and to test the resulting monolayer B films against a monolayer film consisting of 100% amorphous nylon (Selar PA 3426). Secant modulus at 2% elongation of the monolayer film was measured in the machine direction according to ASTM D882-97 at a strain rate of 0.1 in./in.min. Results are shown below in Table 1:

TABLE 1

| Monolayer Film Composition % | | Secant |
|---|---|---|
| Selar PA3426 | Fusabond MN493D | Modulus psi |
| 100 | 0 | 323,500 |
| 85 | 15 | 235,600 |
| 75 | 25 | 190,000 |

The data in Table 1 shows the reduction in modulus resulting from the addition of Fusabond MN493D to Selar PA3426. The lower modulus values indicate that the compounded resins are considerably softer than the control resin of the same thickness with 100% amorphous nylon. The reduction in modulus allows the production of nylon-based mutilayer films which are soft and quiet, as indicated in further examples below.

EXAMPLE 2

A five-layer film was produced in accordance with this invention by coextrusion casting, resulting in a film with a total thickness of 3.3 mil and a barrier layer thickness of 0.32 mil. The film structure was A/B/C/B/A, where A was a polyethylene-based resin (Exact 8201, Exxon Chemical Co.) modified by the addition of 5% of a slip/antiblock concentrate (EXT4226TSE, A. Schulman Co.) and 3% of a low-density polyethylene (LD200.48, Exxon Chemical Co.). B are tie layers consisting of anhydride-modified ethylene vinyl acetate copolymer (Bynel 3861, DuPont Co.), and C is a blend of amorphous nylon (Selar PA3426) with an anhydride-modified ethylene octene copolymer (Fusabond MN493D) at 85% to 15% weight ratio.

The film was tested for quietness by forming a 4 inch by 4 inch sample into a cylinder and mounting it on a test fixture wherein one end of the cylinder was held fixed and the other was rotated around the cylinder axis at an angle of 15 degrees at 70 cycles per minutes. Noise emissions produced by the film's flexing were analyzed with a sound level meter. For comparison, the same test was conducted on a commercial ostomy film with a chlorinated barrier. Results are shown below:

TABLE 2

| Sample | dBA | dB, 8 kHz | dB, 16 kHz |
|---|---|---|---|
| Film of Example 2 | 64 | 49 | 39 |
| Control Film | 74 | 55 | 49 |

In this table, dBA is a weighted average that takes into account the human perception of noise over the entire frequency range, whereas dB values in the 8 and 16 kHz octave bands are indicative of the noise in the higher frequency range and represent the crispness of the noise. The dBA and dB values therefore reveal that the film sample embodying the invention is considerably quieter than the control sample in which the core layer is based on PVDC.

EXAMPLE 3

A five-layer film was produced in accordance with this invention by coextrusion casting, resulting in a film with a total thickness of 3.2 mil and a barrier layer thickness of 0.28 mil. The film construction was A/B/C/B/A, having the same composition as the film of Example 2 except that the tie layers B were polyethylene-based (Bynel 41E557, DuPont Co.). The film was tested for quietness as described in Example 2. Results are shown in the table below which includes a control sample of a commercial ostomy film having a chlorinated barrier layer of PVDC.

TABLE 3

| Sample | dBA | dB, 8 kHz | dB, 16 kHz |
|---|---|---|---|
| Film of Example 3 | 65 | 51 | 45 |
| Control Film | 74 | 55 | 49 |

As in Example 2, the dBA and dB values at 8 and 16 kHz reveal that the film sample of Example 3 is considerably quieter than the control sample in which the core layer is PVDC.

EXAMPLE 4

The film of Examples 2 and 3 were tested for odor transmission using British Standard 7127, Part 101, Appendix G. Method for Determining Odor Transmission of Colostomy and Ileostomy Bag Materials, British Standard Institution, London. Both films passed the test, indicating that the modification of the nylon barrier layer does not have a detrimental effect on odor barrier properties of the films.

In addition, a quantitative test of the barrier properties of the film of Example 2 was conducted using three model compounds for fecal odor: dimethyldisulfide, indole, and skatole. For comparison, the same test was conducted on a commercial ostomy film with a chlorinated (PVDC) barrier layer. Analysis of effluent gases was conducted by gas chromatography using a flame ionization detector. Table 4 shows breakthrough times and concentration of each component in the effluent stream after 60 hours.

TABLE 4

| Film | Breakthrough Times, min | | | Concentration at 60 hours | | |
|---|---|---|---|---|---|---|
| | Dimethyl disulfide min | Indole min | Skatole min | Dimethy disulfidel ppm | Indole ppb | Skatole ppb |
| Film of Example 2 | 2680 | 1880 | 2180 | 25 | 102 | 51 |
| Control Film | 722 | 1140 | 1610 | 137 | 292 | 91 |

Better barrier properties are expected for films that show longer breakthrough times and lower effluent concentration. The film of Example 2 is superior to the chlorinated control film in both respects, indicating superior performance as a barrier to fecal odorants.

EXAMPLE 5

Monolayer film's were prepared by extrusion using a Brabender extruder and Grivory G21 (from EMS-Chemie AG) as the amorphous nylon. Grivory G21 is very similar in properties to Selar PA3426 used in previous examples. The modifier was Lotader 4720 (from Atofina Chemicals, Inc.). As in Example 1, secant modulus at 2% elongation of the monolayer films was measured in the machine direction according to ASTM D882-97 at a strain rate of 0.1 in./in.min. The results shown in Table 5 illustrate the effect of the addition of Lotader 4720 to Grivory G21 monolayer films. The modulus is progressively reduced as the level of Lotader 4720 is increased.

TABLE 5

| Monolayer Film Composition % | | Secant |
|---|---|---|
| Grivory G21 | Lotader 4720 | Modulus psi |
| 100 | 0 | 125,000 |
| 75 | 25 | 65,800 |
| 70 | 30 | 44,300 |
| 65 | 35 | 25,100 |

While in the foregoing, embodiments of the invention have been disclosed in detail for purposes of illustration, it will be understood by those skilled in the art that many of these details may be varied without departing from the spirit and scope of the invention.

The invention claimed is:

1. An ostomy pouch having two side walls, one side wall of which has a stoma-receiving opening formed therein and an attachment means located about said stoma-receiving opening for peristomal attachment of said ostomy pouch to a patient, wherein each of said two side walls comprises a multilayer chlorine-free film having an odor barrier layer co-extruded with at least one heat-sealable skin layer comprising an ethylene polymer or copolymer or blend thereof; the at least one skin layer of the one side wall facing the at least one skin layer of the other side wall, being heat-sealed together along the peripheral edge portions of said ostomy pouch; said odor barrier layer of each side wall comprising about 70% to 90% per total weight of the odor barrier layer of an amorphous polyamide resin, blended with about 10% to 30% per total weight of the odor barrier layer of an anhydride-modified olefinic polymer or copolymer having a density of 0.95 g/cc or lower, in which said odor barrier layer has a secant modulus that is less than that of an unmodified odor barrier layer of the same thickness, of 100% per total weight of the odor barrier layer of the same amorphous polyamide, as measured in accordance with ASTM D882-97.

2. The ostomy pouch of claim 1 in which said olefinic polymer or copolymer of said odor barrier layer is modified with 0.1% to 2% maleic anhydride.

3. The ostomy pouch of claim 1 in which said olefinic polymer or copolymer of said odor barrier layer is an ethylene alpha olefin copolymer modified with about 0.5% maleic anhydride.

4. The ostomy pouch of claim 3 in which two of said skin layers and two adhesive tie layers are provided on opposite sides of said odor barrier layer, said adhesive tie layers being immediately adjacent to said odor barrier layer.

5. The ostomy pouch of claim 4 in which said skin layers consist essentially of polyethylene or a copolymer of ethylene.

6. The ostomy pouch of claim 4 in which each of said adhesive tie layers consists essentially of anhydride-modified polyethylene or anhydride-modified ethylene vinyl acetate copolymer.

7. The ostomy pouch of claim 4 in which said odor barrier layer of each film has a thickness within the range of about 0.2 mil to 0.3 mil and the total thickness of each film is within the range of about 3 mil to 4 mil.

8. The ostomy pouch of claim 1 in which said olefinic polymer or copolymer of said odor barrier layer is a copolymer of ethylene with at least one ester containing comonomer and 0.1% to 2% maleic anhydride.

9. The ostomy pouch of claim 8 in which said ester-containing comonomer is ethyl acrylate.

10. The ostomy pouch of claim 1 in which said amorphous polyamide resin in said odor barrier layer of each film is the condensation product of hexamethylenediamine, terephthalic acid, and isophthalic acid, and in which 65% to 80% of the polyamide units are derived from hexamethylene isophthalamide.

11. The ostomy pouch of claim 1 in which said anhydride-modified olefinic polymer or copolymer is present in the range of 15% to 25% per total weight odor barrier layer.

* * * * *